United States Patent
Doering et al.

(10) Patent No.: US 10,413,492 B2
(45) Date of Patent: Sep. 17, 2019

(54) ANTIPERSPIRANT STICK

(71) Applicant: Henkel AG & Co. KGaA, Duesseldorf (DE)

(72) Inventors: Thomas Doering, Dormagen (DE); Stefanie Schmitz, Moenchengladbach (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 16/037,830

(22) Filed: Jul. 17, 2018

(65) Prior Publication Data

US 2019/0021964 A1    Jan. 24, 2019

(30) Foreign Application Priority Data

Jul. 18, 2017   (DE) .................. 10 2017 212 293

(51) Int. Cl.
| | | |
|---|---|---|
| *A61K 8/26* | (2006.01) | |
| *A61K 8/28* | (2006.01) | |
| *A61K 8/891* | (2006.01) | |
| *A61Q 15/00* | (2006.01) | |
| *A61K 8/34* | (2006.01) | |
| *A61K 8/02* | (2006.01) | |
| *A61K 8/37* | (2006.01) | |

(52) U.S. Cl.
CPC .............. *A61K 8/26* (2013.01); *A61K 8/0229* (2013.01); *A61K 8/28* (2013.01); *A61K 8/342* (2013.01); *A61K 8/37* (2013.01); *A61K 8/891* (2013.01); *A61Q 15/00* (2013.01)

(58) Field of Classification Search
CPC .......... A61K 8/37; A61K 8/0229; A61K 8/28; A61K 8/891; A61Q 15/00
See application file for complete search history.

(56) References Cited

U.S. PATENT DOCUMENTS

| | | | |
|---|---|---|---|
| 6,074,632 A | 6/2000 | Shen | |
| 2002/0034481 A1* | 3/2002 | Bianchi | A61K 8/0229 424/65 |
| 2009/0304617 A1* | 12/2009 | Banowski | A61K 8/02 424/68 |

FOREIGN PATENT DOCUMENTS

| | | |
|---|---|---|
| WO | 9827939 A2 | 7/1998 |
| WO | 0211691 A1 | 2/2002 |
| WO | 2006119981 A1 | 11/2006 |

* cited by examiner

*Primary Examiner* — Andrew S Rosenthal
(74) *Attorney, Agent, or Firm* — Lorenz & Kopf, LLP

(57) ABSTRACT

Antiperspirant sticks containing
(A) at least one perspiration-inhibiting substance from the group formed by aluminum or aluminum-zirconium salts
(B) at least one hydrophobic carrier material
(C) behenyl behenate
(D) behenate from the group formed by cetyl behenate and stearyl behenate,
wherein the ratio of the proportion by weight of the behenyl behenate (C) with respect to the total weight of the antiperspirant stick to the proportion by weight of the behenate from the group formed by cetyl behenate and stearyl behenate with respect to the total weight of the antiperspirant stick is 4:1 to 1:4, and a method employing said antiperspirant sticks.

15 Claims, No Drawings

ANTIPERSPIRANT STICK

CROSS-REFERENCE TO RELATED APPLICATION

This application claims priority to German Patent Application No. 10 2017 212 293.5, filed Jul. 18, 2017, which is incorporated herein by reference in its entirety.

TECHNICAL FIELD

The present application relates to cosmetic and dermatological antiperspirant sticks with improved chemical and physical stability and improved perspiration-inhibiting activity.

BACKGROUND

Compositions for combatting body odour are an important component of daily personal hygiene. They are supposed to ensure that perspiration formed during the course of the day due to various activities (moving the body, work, sport), and also during psychological stress, does not give rise to unpleasant body odour.

The multiple components of perspiration and the multiple causes of body odour development are matched by the multiple deodorizing substances in commercial deodorants. Substances which may be used as cosmetic deodorizing substances are odour absorbers, fragrances, ion exchangers with deodorizing activity, bacteriostatic agents, probiotic components as well as enzyme inhibitors. Put simply, body odour can be caused by the bacteria decomposition of the organic components of perspiration. In turn, some of the typical bacteria found in the natural microflora of human skin are responsible for bacterial decomposition, in particular gram-positive anaerobic cocci, for example staphylococci, such as Staphylococcus hominis, and corynebacteria. Because body odour arises because of bacterial activity, it can be inhibited particularly effectively using cosmetic agents (soaps, creams, powder, sticks, roll-ons, gels or sprays) which contain antimicrobially effective materials and perfume oil compositions.

Aerosol sprays, roll-ons and antiperspirant sticks have become well-established application forms for said compositions. Furthermore, deodorant in powder form (also as a compressed powder) or deodorant applied to a disposable substrate (such as a towel, pad or ball) are also known. A particularly pleasant form of application is known to the person skilled in the art as an antiperspirant stick or cream stick (soft solids). This should be understood to mean viscous compositions which have a creamy texture and which, before application, are pressed through one or more openings of a dispensing portion of an applicator.

Antiperspirant sticks are usually produced in a water-depleted or anhydrous manner. Anhydrous production is then particularly preferred over aqueous systems when a particularly high perspiration-inhibiting activity is desired, because particularly effective perspiration-inhibiting substances such as activated aluminium chlorohydrate are not stable in the long term in aqueous media.

In water-depleted, preferably anhydrously produced antiperspirants, producing a stable active composition and producing optimal application properties constitute a very particular challenge. Anhydrous antiperspirant sticks can, for example, be produced by suspending perspiration-inhibiting aluminium salts in a thickened oily phase. Sticks of this type, however, frequently have insufficient physical stability (syn-aeresis). This phenomenon can be countered by adding supplemental thickeners, but adding such thickeners results in an unwanted high stick hardness which then has disadvantageous effects on the payout properties of the stick.

In the light of this technical background, the technical problem was to provide an antiperspirant in stick form which has high physical stability in addition to outstanding cosmetic application properties.

BRIEF SUMMARY

This disclosure provides an antiperspirant stick including (A) at least one perspiration-inhibiting substance from the group formed by aluminium or aluminium-zirconium salts, (B) at least one hydrophobic carrier material, (C) behenyl behenate, and (D) behenate from the group formed by cetyl behenate and stearyl behenate, wherein the ratio of the proportion by weight of the behenyl behenate (C) with respect to the total weight of the antiperspirant stick to the proportion by weight of the behenate from the group formed by cetyl behenate and stearyl behenate (D) with respect to the total weight of the antiperspirant stick is from about 4:1 to about 1:4.

This disclosure also provides an antiperspirant stick including, with respect to its total weight, (A) from about 5.0% to about 20% by weight of aluminium zirconium trichlorohydrex glycine, (B) hydrophobic carrier material, including from about 30% to about 50% by weight of decamethylcyclopentasiloxane, from about 16% to about 27% by weight of fatty alcohol from the group formed by stearyl alcohol, cetyl alcohol and arachidyl alcohol, from about 12% to about 18% by weight of PPG-14 butyl ether, (C) from about 0.3% to about 1.0% by weight of behenyl behenate, and (D) from about 0.3% to about 1.0% by weight of behenate from the group formed by cetyl behenate and stearyl behenate, wherein the ratio of the proportion by weight of the behenyl behenate (C) with respect to the total weight of the antiperspirant stick to the proportion by weight of behenate from the group formed by cetyl behenate and stearyl behenate (D) with respect to the total weight of the antiperspirant stick is from about 2:1 to about 1:2.

DETAILED DESCRITPION

The following detailed description is merely exemplary in nature and is not intended to limit the disclosure or the application and uses of the subject matter as described herein. Furthermore, there is no intention to be found by any theory presented in the preceding backgroud or the following detailed description.

The aforementioned technical problem has surprisingly been solved by employing an antiperspirant stick based on a suspension of a perspiration-inhibiting substance in a hydrophobic carrier material to which, as further substances, a mixture of behenyl behenate and cetyl behenate or stearyl behenate has been added.

The subject matter of the application is exemplified by the following points:

An antiperspirant stick, containing
(A) at least one perspiration-inhibiting substance from the group formed by aluminium or aluminium-zirconium salts
(B) at least one hydrophobic carrier material
(C) behenyl behenate
(D) behenate from the group formed by cetyl behenate and stearyl behenate, wherein the ratio of the proportion by weight of the behenyl behenate (C) with respect to the total weight of the antiperspirant stick to the proportion by weight of the behenate from the group formed by cetyl behenate and stearyl behenate (D) with respect to the total weight of the antiperspirant stick is from about 4:1 to about 1:4.

The antiperspirant stick according to point 1, wherein the ratio of the proportion by weight of the behenyl behenate (C) with respect to the total weight of the antiperspirant stick to the proportion by weight of cetyl behenate and/or stearyl behenate (D) with respect to the total weight of the antiperspirant stick is from about 2:1 to about 1:2 and in particular from about 4:3 to about 3:4.

The antiperspirant stick according to one of the preceding points, wherein the stick contains, as the perspiration-inhibiting substance, at least one perspiration-inhibiting aluminium-zirconium salt selected from the groups formed by
(i) water-soluble astringent inorganic aluminium-zirconium salts, in particular aluminium zirconium trichlorohydrate, aluminium zirconium tetrachlorohydrate, aluminium zirconium pentachlorohydrate, aluminium zirconium octachlorohydrate;
(ii) water-soluble astringent organic aluminium-zirconium salts, in particular aluminium zirconium propylene glycol complexes, aluminium zirconium trichlorohydrex glycine, aluminium zirconium tetrachlorohydrex glycine, aluminium zirconium pentachlorohydrex glycine, aluminium zirconium octachlorohydrex glycine; as well as
(iii) mixtures thereof.

The antiperspirant stick according to one of the preceding points, wherein the proportion by weight of the perspiration-inhibiting substance with respect to the total weight of the antiperspirant stick is from about 0.1% to about 35% by weight, preferably from about 2.0% to about 25% by weight and in particular from about 5.0% to about 20% by weight.

The antiperspirant stick according to one of the preceding points, wherein the hydrophobic carrier material is from the group formed by thickened oils, preferably thickened silicone oils.

The antiperspirant stick according to one of the preceding points, wherein the hydrophobic carrier material comprises at least one compound from the group formed by silicone oils, in particular
    octamethylcyclotetrasiloxane, decamethylcyclopentasiloxane, dodecamethylcyclohexasiloxane, hexamethyldisiloxane, octamethyltrisiloxane and decamethyltetrasiloxane as well as mixtures thereof
    mixtures formed from decamethylcyclopentasiloxane and dodecamethylcyclohexasiloxane
    mixtures formed from hexamethyldisiloxane, octamethyltrisiloxane and decamethyltetrasiloxane
    particularly preferably, decamethylcyclopentasiloxane.

7. The antiperspirant stick according to point 6, wherein the proportion by weight of the hydrophobic carrier material from the group formed by silicone oils with respect to the total weight of the antiperspirant stick is from about 25% to about 60% by weight, preferably from about 30% to about 50% by weight and in particular from about 35% to about 45% by weight.

The antiperspirant stick according to one of the preceding points, wherein the hydrophobic carrier material comprises at least one compound from the group formed by fatty alcohols, preferably from saturated C10-C22 fatty alcohols, in particular from fatty alcohols from the group formed by stearyl alcohol, cetyl alcohol and arachidyl alcohol.

The antiperspirant stick according to point 8, wherein the proportion by weight of the hydrophobic carrier material from the group formed by fatty alcohols with respect to the total weight of the antiperspirant stick is from about 12% to about 35% by weight, preferably from about 15% to about 30% by weight and in particular from about 16% to about 27% by weight.

The antiperspirant stick according to one of the preceding points, wherein the hydrophobic carrier material comprises at least one compound from the group formed by addition products of at least about 6 ethylene oxide and/or propylene oxide units to mono- or multivalent C3-22 alkanols, preferably from the group formed by addition products of at least about 6 propylene oxide units to butanol, in particular from the group formed by PPG-14 butyl ether.

The antiperspirant stick according to point 9, wherein the proportion by weight of the hydrophobic carrier material from the group formed by addition products of at least about 6 ethylene oxide and/or propylene oxide units to mono- or multivalent C3-22 alkanols with respect to the total weight of the antiperspirant stick is from about 8.0% to about 24% by weight, preferably from about 10% to about 21% by weight and in particular from about 12% to about 18% by weight.

The antiperspirant stick according to one of the preceding points, wherein the proportion by weight of behenyl behenate with respect to the total weight of the antiperspirant stick is from about 0.1% to about 4.0% by weight, preferably from about 0.2% to about 2.0% by weight and in particular from about 0.3% to about 1.0% by weight.

The antiperspirant stick according to one of the preceding points, wherein the proportion by weight of the total weight of cetyl behenate and stearyl behenate with respect to the total weight of the antiperspirant stick is from about 0.1% to about 4.0% by weight, preferably from about 0.2% to about 2.0% by weight and in particular from about 0.3% to about 1.0% by weight.

An antiperspirant stick containing, with respect to its total weight,
(A) from about 5.0% to about 20% by weight of aluminium zirconium trichlorohydrex glycine
(B) hydrophobic carrier material, comprising
    from about 30% to about 50% by weight of decamethylcyclopentasiloxane
    from about 16% to about 27% by weight of fatty alcohol from the group formed by stearyl alcohol, cetyl alcohol and arachidyl alcohol
    from about 12% to about 18% by weight of PPG-14 butyl ether
(C) from about 0.3% to about 1.0% by weight of behenyl behenate
(D) from about 0.3% to about 1.0% by weight of behenate from the group formed by cetyl behenate and stearyl behenate,
wherein the ratio of the proportion by weight of the behenyl behenate (C) with respect to the total weight of the antiperspirant stick to the proportion by weight of the behenate from the group formed by cetyl behenate and stearyl behenate (D) with respect to the total weight of the antiperspirant stick is from about 2:1 to about 1:2.

A non-therapeutic, cosmetic method for reducing and/or regulating the formation of perspiration and/or of body odour, in which a composition according to one of points 1 to 14 is applied to the skin in an effective quantity, preferably to the skin in the region of the armpit.

Antiperspirant sticks as contemplated herein contain
(A) at least one perspiration-inhibiting substance from the group formed by aluminium or aluminium-zirconium salts (B) at least one hydrophobic carrier material
(C) behenyl behenate
(D) behenate from the group formed by cetyl behenate and stearyl behenate,
wherein the ratio of the proportion by weight of the behenyl behenate (C) with respect to the total weight of the antiperspirant stick to the proportion by weight of the behenate from the group formed by cetyl behenate and stearyl behenate (D) with respect to the total weight of the antiperspirant stick is from about 4:1 to about 1:4. The weight ratio of behenyl behenate (C) to cetyl behenate and stearyl behenate (D) sets the ratio of the proportion by weight of the behenyl behenate (C) to the proportion by weight of cetyl behenate and stearyl behenate (D). In this manner, the antiperspirant stick may contain exclusively cetyl behenate or exclusively stearyl behenate as the behenate (D), or a mixture of cetyl behenate and stearyl behenate. Preferred antiperspirant sticks contain mixtures of cetyl behenate and stearyl behenate.

By adding behenyl behenate, cetyl behenate and stearyl behenate in specific proportions by weight, surprisingly, the sticks are physically stabilized, suppressing synaeresis of the stick matrix and improving the application properties of the antiperspirant onto the skin, and even improving the payout quantity as well as the glide properties of the sticks on the skin. The physical stability and the application properties have proved to be particularly advantageous when the ratio of the proportion by weight of the behenyl behenate (C) with respect to the total weight of the antiperspirant stick to the proportion by weight of the behenate from the group formed by cetyl behenate and stearyl behenate (D) is from about 2:1 to about 1:2 and in particular from about 4:3 to about 3:4.

Particularly preferred antiperspirant sticks contain
(A) at least one perspiration-inhibiting substance from the group formed by aluminium or aluminium-zirconium salts
(B) at least one hydrophobic carrier material
(C) behenyl behenate
(D) cetyl behenate and stearyl behenate,
wherein the ratio of the proportion by weight of the behenyl behenate (C) with respect to the total weight of the antiperspirant stick to the proportion by weight of cetyl behenate and stearyl behenate (D) with respect to the total weight of the antiperspirant stick is from about 4:1 to about 1:4, preferably from about 2:1 to about 1:2 and in particular from about 4:3 to about 3:4.

The proportion by weight of the behenyl behenate with respect to the total weight of the antiperspirant stick is preferably from about 0.1% to about 4.0% by weight, preferably from about 0.2% to about 2.0% by weight and in particular from about 0.3% to about 1.0% by weight, while the proportion by weight of the total weight of cetyl behenate and stearyl behenate with respect to the total weight of the antiperspirant stick is preferably from about 0.1% to about 4.0% by weight, preferably from about 0.2% to about 2.0% by weight and in particular from about 0.3% to about 1.0% by weight.

The first essential component of the antiperspirant sticks is at least one perspiration-inhibiting substance from the group formed by aluminium or aluminium-zirconium salts.

Preferred antiperspirant substances are selected from water-soluble astringent inorganic and organic salts of aluminium and zirconium or any mixtures of these salts. As contemplated herein, the term "water solubility" means a solubility of at least about 3% by weight at about 20° C., which means that quantities of at least about 3 g of the antiperspirant substance are soluble in about 97 g of water at about 20° C. Preferably and as contemplated herein, the term "solubility in water" means a solubility of at least about 5% by weight at about 20° C., which means that quantities of at least about 5 g of the antiperspirant substance are soluble in about 95 g of water at about 20° C.

Particularly preferred antiperspirant substances are selected from aluminium chlorohydrate, in particular aluminium chlorohydrate with the general formula $[Al_2(OH)_5Cl.1-6H_2O]_n$, preferably $[Al_2(OH)_5Cl.2-3H_2O]_n$, which may be present in the non-activated or in the activated (depolymerized) form, as well as aluminium chlorohydrate with the general formula $[Al_2(OH)_4Cl_2.1-6H_2O]_n$, preferably $[Al_2(OH)_4Cl_2.2-3H_2O]_n$, which may be present in the non-activated or in the activated (depolymerized) form.

Even more preferred substances are aluminium sesquichlorohydrate, aluminium dichlorohydrate, aluminium chlorohydrex propylene glycol (PG) or aluminium chlorohydrex polyethylene glycol (PEG), aluminium or aluminium-zirconium-glycol complexes, for example aluminium or aluminium-zirconium-propylene glycol complexes, aluminium sesquichlorohydrex-PG or aluminium sesquichlorohydrex-PEG, aluminium PG-dichlorohydrex or aluminium PEG-dichlorohydrex, aluminium hydroxide, furthermore selected from aluminium zirconium chlorohydrates, such as aluminium zirconium trichlorohydrate, aluminium zirconium tetrachlorohydrate, aluminium zirconium pentachlorohydrate, aluminium zirconium octachlorohydrate, aluminium-zirconium-chlorohydrate-glycine complexes such as aluminium zirconium trichlorohydrex glycine, aluminium zirconium tetrachlorohydrex glycine, aluminium zirconium pentachlorohydrex glycine, aluminium zirconium octachlorohydrex glycine, potassium aluminium sulphate ($KAl(SO_4)_2.12H_2O$, alum), dehydrated alum ($KAl(SO_4)_2$ containing from about zero to about 11 mol of water of crystallization), sodium aluminium chlorhydroxy lactate, aluminium bromohydrate, aluminium chloride, aluminium sulphate, aluminium lactate, sodium aluminium chlorhydroxy lactate, zirconyl oxyhalides, in particular zirconyl oxychlorides, zirconyl hydroxyhalides, in particular zirconyl hydroxychlorides (zirconium chlorohydrate).

Particularly preferred antiperspirant substances as contemplated herein are selected from what are known as "activated" aluminium and aluminium-zirconium salts which are also known as antiperspirant substances "with enhanced activity". Substances of this type are known in the prior art and are also commercially available. Activated aluminium and aluminium-zirconium salts are usually produced by heat treatment of a relatively dilute solution of the salt (for example, approximately 10% by weight of salt), in order to enlarge its HPLC from about peak 4 to about peak 3 area ratio. The activated salt can then be dried to a powder, in particular by spray drying. In addition to spray drying, roll drying is also suitable, for example. Activated aluminium and aluminium-zirconium salts typically have a HPLC from about peak 4 to about peak 3 area ratio of at least about 0.4, preferably at least about 0.7, particularly preferably at least about 0.9, wherein at least about 70% of the aluminium can be assigned to this peak.

Further preferred perspiration-inhibiting substances are basic calcium-aluminium salts. These salts are produced by reacting calcium carbonate with aluminium chlorohydrate or aluminium chloride and aluminium powder or by adding calcium chloride dihydrate to aluminium chlorohydrate.

Further preferred perspiration-inhibiting substances are aluminium-zirconium complexes, which are buffered with salts of amino acids, in particular with alkali and alkaline-earth glycinates. Further preferred perspiration-inhibiting substances are activated aluminium or aluminium-zirconium salts, containing from about 5 to about 78% by weight (USP) of an activated perspiration-inhibiting aluminium or aluminium-zirconium salt, an amino acid or hydroxyalkanoic acid in a quantity such as to produce an (amino acid or hydroxyalkanoic acid) to (Al+Zr) ratio by weight of from about 2:1 to about 1:20 and preferably from about 1:1 to about 1:10, as well as a soluble calcium salt in a quantity such as to produce a Ca:(Al+Zr) ratio by weight of from about 1:1 to about 1:28 and preferably from about 1:2 to about 1:25. Particularly preferred solid activated perspiration-inhibiting salt compositions contain from about 48 to about 78% by weight (USP), preferably from about 66 to about 75% by weight, of an activated aluminium or aluminium-zirconium salt and from about 1 to about 16% by weight, preferably from about 4 to about 13% by weight, of molecularly bound water (water of hydration), furthermore that amount of calcium salt which produces a Ca:(Al+Zr) ratio by weight of from about 1:1 to about 1:28, preferably from about 1:2 to about 1:25, and that amount of amino acid which produces an amino acid to (Al+Zr) ratio by weight of from about 2:1 to about 1:20, preferably from about 1:1 to about 1:10.

Further particularly preferred solid perspiration-inhibiting activated salt compositions contain from about 48 to about 78% by weight (USP), preferably from about 66 to about 75% by weight, of an activated aluminium or aluminium-zirconium salt and from about 1 to about 16% by weight, preferably from about 4 to about 13% by weight, of molecularly bound water (water of hydration), furthermore that amount of water-soluble calcium salt which produces a Ca:(Al+Zr) ratio by weight of form about 1:1 to about 1:28, preferably from about 1:2 to about 1:25, and that amount of glycine which produces a glycine to (Al+Zr) ratio by weight of from about 2:1 to about 1:20, preferably from about 1:1 to about 1:10.

Further particularly preferred solid perspiration-inhibiting activated salt compositions contain from about 48 to about 78% by weight (USP), preferably from about 66 to about 75% by weight, of an activated aluminium or aluminium-zirconium salt and from about 1 to about 16% by weight, preferably from about 4 to about 13% by weight, of molecularly bound water, furthermore that amount of calcium salt which produces a Ca:(Al+Zr) ratio by weight of from about 1:1 to about 1:28, preferably from about 1:2 to about 1:25, and that amount of hydroxyalkanoic acid which produces a hydroxyalkanoic acid to (Al+Zr) ratio by weight of from about 2:1 to about 1:20, preferably from about 1:1 to about 1:10.

In order to stabilize the perspiration-inhibiting salts, preferred water-soluble calcium salts are selected from calcium chloride, calcium bromide, calcium nitrate, calcium citrate, calcium formate, calcium acetate, calcium gluconate, calcium ascorbate, calcium lactate, calcium glycinate, calcium carbonate, calcium sulphate, calcium hydroxide, as well as mixtures thereof.

In order to stabilize the perspiration-inhibiting salts, preferred amino acids are selected from glycine, alanine, leucine, isoleucine, β-alanine, valine, cysteine, serine, tryptophan, phenylalanine, methionine, β-amino-n-butanoic acid and γ-amino-n-butanoic acid and salts thereof, each in the d-form, the l-form and the dl-form; glycine is particularly preferred.

In order to stabilize the perspiration-inhibiting salts, preferred hydroxyalkanoic acids are selected from glycolic acid and lactic acid.

Further preferred perspiration-inhibiting substances are activated aluminium or aluminium-zirconium salts containing from about 5 to about 78% by weight (USP) of an activated perspiration-inhibiting aluminium or aluminium-zirconium salt, an amino acid or hydroxyalkanoic acid in a quantity such as to produce an (amino acid or hydroxyalkanoic acid) to (Al+Zr) ratio by weight of from about 2:1 to about 1:20 and preferably from about 1:1 to about 1:10, as well as a water-soluble strontium salt in a quantity such as to produce a Sr:(Al+Zr) ratio by weight of from about 1:1 to about 1:28 and preferably from about 1:2 to about 1:25.

Particularly preferred solid perspiration-inhibiting activated salt compositions contain from about 48 to about 78% by weight (USP), preferably from about 66 to about 75% by weight, of an activated aluminium or aluminium-zirconium salt and from about 1 to about 16% by weight, preferably from about 4 to about 13% by weight, of molecularly bound water, furthermore that amount of water-soluble strontium salt which produces the Sr:(Al+Zr) ratio by weight of from about 1:1 to about 1:28, preferably from about 1:2 to about 1:25, and that amount of amino acid which produces the amino acid to (Al+Zr) ratio by weight of from about 2:1 to about 1:20, preferably from about 1:1 to about 1:10.

Further particularly preferred solid perspiration-inhibiting activated salt compositions contain from about 48 to about 78% by weight (USP), preferably from about 66 to about 75% by weight, of an activated aluminium or aluminium-zirconium salt and from about 1 to about 16% by weight, preferably from about 4 to about 13% by weight, of molecularly bound water, furthermore that amount of water-soluble strontium salt which produces the Sr:(Al+Zr) ratio by weight of from about 1:1 to about 1:28, preferably from about 1:2 to about 1:25, and that amount of glycine which produces the glycine to (Al+Zr) ratio by weight of from about 2:1 to about 1:20, preferably from about 1:1 to about 1:10.

Further particularly preferred solid perspiration-inhibiting activated salt compositions contain from about 48 to about 78% by weight (USP), preferably from about 66 to about 75% by weight, of an activated aluminium or aluminium-zirconium salt and from about 1 to about 16% by weight, preferably from about 4 to about 13% by weight, of molecularly bound water, furthermore that amount of water-soluble strontium salt which produces the Sr:(Al+Zr) ratio by weight of from about 1:1 to about 1:28, preferably from about 1:2 to about 1:25, and that amount of hydroxyalkanoic acid which produces the hydroxyalkanoic acid to (Al+Zr) ratio by weight of from about 2:1 to about 1:20, preferably from about 1:1 to about 1:10.

Further preferred activated aluminium salts are those with general formula $Al_2(OH)_{6-a}Xa$, in which X is Cl, Br, I or $NO_3$ and "a" has a value of from about 0.3 to about 5, preferably from about 0.8 to about 2.5 and particularly preferably from about 1 to about 2, which produces a molar ratio Al:X of from about 0.9:1 to about 2.1:1, as disclosed, for example, in U.S. Pat. No. 6,074,632. In these salts, some water of hydration is generally associatively bound, typically from about 1 to about 6 mol of water per mol of salt. Aluminium chlorohydrate (i.e. X is Cl in the above formula) and in particular 5/6-basic aluminium chlorohydrate, wherein "a" is 1, which produces a molar ratio of aluminium to chlorine of from about 1.9:1 to about 2.1:1, is particularly preferred. Particularly preferred zirconium-free aluminium sesquichlorohydrates as contemplated herein have a molar metal-to-chloride ratio of from about 1.5:1 to about 1.8:1.

Preferred activated aluminium-zirconium salts are those which constitute mixtures or complexes of the aluminium salts described above with zirconium salts with formula $ZrO(OH)_{2-pb}Y_b$, in which Y is Cl, Br, I, $NO_3$ or $SO_4$, b is a rational number from about 0.8 to about 2 and p has the value of Y, as disclosed, for example, in U.S. Pat. No. 6,074,632. In these zirconium salts, some water of hydration is generally associatively bound, typically from about 1 to about 7 mol of water per mol of salt. Preferably, the zirconium salt is zirconyl hydroxychloride with formula $ZrO(OH)_{2-b}Cl_b$, in which b is a rational number from about 0.8 to about 2, preferably from about 1.0 to about 1.9. Preferred aluminium-zirconium salts have a Al:Zr molar ratio of from about 2 to about 10 and a metal:(X+Y) ratio of from about 0.73 to about 2.1, preferably from about 0.9 to about 1.5. A particularly preferred salt is aluminium zirconium chlorohydrate (i.e., X and Y are Cl), which has an Al:Zr ratio of from about 2 to about 10 and a molar metal:Cl ratio of from about 0.9 to about 2.1. The term "aluminium zirconium chlorohydrate" encompasses the tri-, tetra-, penta- and octachlorohydrate forms.

Preferred zirconium salts as contemplated herein have the general formula $ZrO(OH)_{2-a}Cl_a \cdot xH_2O$ with a=1.5-1.87; x=1-7, in which a and x are rational numbers.

Preferred aluminium-zirconium salts have a molar metal-to-chloride ratio of from about 0.9 to about 1.3, preferably from about 0.9 to about 1.1, particularly preferably, from about 0.9 to about 1.0.

Preferred aluminium zirconium chlorohydrates generally have the empirical formula $AlnZr(OH)[_{3n}+4-m(n+1)](Cl)[m(n+1)]$ with n=2.0-10.0, preferably 3.0-8.0, m=0.77-1.11 (corresponds to a molar metal (Al+Zr)-to-chloride ratio of 1.3-0.9), preferably m=0.91-1.11 (corresponds to M:Cl=1.1-0.9), and particularly preferably, m=1.00-1.11 (corresponds to M:Cl=1.0-0.9), yet more preferably m=1.02-1.11 (corresponds to M:Cl=0.98-0.9) as well as highly preferably, m=1.04-1.11 (corresponds to M:Cl=0.96-0.9).

In general, some water of hydration is associatively bound with these salts, typically from about 1 to about 6 mol of water per mol of salt, corresponding to from about 1 to about 16% by weight, preferably from about 4 to about 13% by weight of water of hydration.

Normally, the preferred aluminium zirconium chlorohydrates are associated with an amino acid in order to inhibit polymerization of the zirconium species during production. Preferred stabilizing amino acids are selected from glycine, alanine, leucine, isoleucine, β-alanine, valine, cysteine, serine, tryptophan, phenylalanine, methionine, β-amino-n-butanoic acid and γ-amino-n-butanoic acid and salts thereof, each in the d-form, the l-form and the dl-form; glycine is particularly preferred. The amino acid is present in an amount of from about 1 to about 3 Mol, preferably from about 1.3 to about 1.8 Mol, respectively per mol of zirconium in the salt.

Preferred perspiration-inhibiting salts are aluminium zirconium tetrachlorohydrate (Al:Zr=2-6; M:Cl=0.9-1.3), in particular salts with a molar metal-to-chloride ratio of from about 0.9 to about 1.1, preferably from about 0.9 to about 1.0.

Aluminium zirconium chlorohydrate-glycine salts stabilized with betaine $((CH_3)_3N+\!\!-\!\!CH_2\!\!-\!\!COO-)$ are more preferred as contemplated herein. Particularly preferred corresponding compounds have a molar total (betaine+glycine)/Zr ratio of (from about 0.1 to about 3.0):1, preferably (from about 0.7 to about 1.5):1, and a molar ratio of betaine to glycine of at least about 0.001:1. A particularly effective embodiment of an antiperspirant salt as contemplated herein contains what is known as an "activated" salt, in particular a salt with a high HPLC peak 5 aluminium content, in particular with a peak 5 area of at least about 33%, particularly preferably at least about 45%, with respect to the total area under peaks from about 2 to about 5, measured by HPLC of an about 10% by weight aqueous solution of the substance under conditions under which the aluminium species are resolved into at least about 4 successive peaks (denoted as peaks from about 2 to about 5).

Furthermore, activated salts of the "ESAZCH" type are preferred, which have an HPLC from about peak 4 to about peak 3 area ratio of at least about 0.4, preferably at least about 0.7, particularly preferably at least about 0.9.

Further particularly preferred antiperspirant substances are those aluminium-zirconium salts with a high HPLC peak 5 aluminium content, which are additionally stabilized with a water-soluble strontium salt and/or with a water-soluble calcium salt.

In summary, antiperspirant sticks which have proved to be particularly advantageous from a cosmetic viewpoint are those which contain, as the perspiration-inhibiting substance, at least one perspiration-inhibiting aluminium-zirconium salt selected from the groups formed by (i) water-soluble astringent inorganic aluminium-zirconium salts, in particular aluminium zirconium trichlorohydrate, aluminium zirconium tetrachlorohydrate, aluminium zirconium pentachlorohydrate, aluminium zirconium octachlorohydrate;

(ii) water-soluble astringent organic aluminium-zirconium salts, in particular aluminium zirconium propylene glycol complexes, aluminium zirconium trichlorohydrex glycine, aluminium zirconium tetrachlorohydrex glycine, aluminium zirconium pentachlorohydrex glycine, aluminium zirconium octachlorohydrex glycine; as well as (iii) mixtures thereof.

Although the antiperspirant sticks can contain the perspiration-inhibiting substance in any concentration, these sticks can nevertheless be optimized as regards their ratios of substance concentration and cosmetic effect. In this regard, proportions by weight of the perspiration-inhibiting substance in the range from about 0.1% to about 35% by weight with respect to the cosmetic action and the physical stability have proved to be particularly advantageous. The proportion by weight of the perspiration-inhibiting substance with respect to the total weight of the antiperspirant stick is thus preferably from about 0.1% to about 35% by weight, particularly preferably from about 2.0% to about 25% by weight and in particular from about 5.0% to about 20% by weight.

The antiperspirant sticks contain hydrophobic carrier material as the second essential component. This hydrophobic carrier material may be a single substance or a mixture of substances. The use of mixtures of substances has been shown to be of particular practical application having regard to adjusting the cosmetic properties and application properties of the sticks.

Preferably, a thickened oil is used as the hydrophobic carrier material, particularly preferably a thickened silicone oil. The term "oil" means an organic substance which is liquid under normal conditions and which is immiscible with water.

Cosmetic oils can be classified into volatile and non-volatile oils. "Non-volatile oils" should be understood to mean those oils which have a vapour pressure of less than about 2.66 Pa (0.02 mm Hg) at about 20° C. and at an atmospheric pressure of 1013 hPa. "Volatile oils" should be understood to mean those oils which have a vapour pressure of from about 2.66 Pa to about 40000 Pa (from about 0.02 mm to about 300 mm Hg), preferably from about 12 to about 12000 Pa (from about 0.1 to about 90 mm Hg), particularly preferably from about 13 to about 8000 Pa, and highly preferably from about 30 to about 3000 Pa, even more preferably from about 100 to about 400 Pa at about 20° C. and at an atmospheric pressure of about 1013 hPa.

Preferred volatile silicone oils are selected from dialkyl and alkylarylsiloxanes, which have a vapour pressure of less than about 2.66 Pa (about 0.02 mm Hg) at about 20° C. and at an atmospheric pressure of about 1013 hPa such as, for example, octamethylcyclotetrasiloxane, decamethylcyclopentasiloxane, dodecamethylcyclohexasiloxane, dimethylpolysiloxane, low molecular weight phenyl trimethicone and methylphenylpolysiloxane, but also hexamethyldisiloxane, octamethyltrisiloxane and decamethyltetrasiloxane. Volatile silicone oils which are cyclic are particularly preferred, such as, for example, octamethylcyclotetrasiloxane, decamethylcyclopentasiloxane and dodecamethylcyclohexasiloxane, as well as mixtures thereof, such as those contained in the commercially available products DC 244, 245, 344 and 345 from Dow Corning.

Volatile silicone oils with from about 2 to about 10 siloxane units are also particularly preferred, in particular hexamethyldisiloxane (L2), octamethyltrisiloxane (L3), decamethyltetrasiloxane (L4) as well as any binary and tertiary mixtures of L2, L3 and/or L4, preferably mixtures such as those which are contained, for example, in the commercially available products DC 2-1184, Dow Corning® 200 (about 0.65 cSt) and Dow Corning® 200 (about 1.5 cSt) from Dow Corning. A further preferred volatile silicone oil is a low molecular weight phenyl trimethicone with a vapour pressure of approximately 2000 Pa at about 20° C., such as that obtainable, for example, from GE Bayer Silicones/Momentive with the name Baysilone Fluid PD 5.

Volatile silicone oils are extremely suitable as carrier oils for antiperspirant compositions as contemplated herein, because they provide a pleasant skin feel with little soiling of textiles.

In summary, those antiperspirant sticks which are preferred on the basis of their cosmetic action and their application properties are those which contain, as the hydrophobic carrier material, at least one compound from the group formed by silicone oils, in particular octamethylcyclotetrasiloxane, decamethylcyclopentasiloxane, dodecamethylcyclohexasiloxane, hexamethyldisiloxane, octamethyltrisiloxane and decamethyltetrasiloxane as well as mixtures thereof mixtures formed from decamethylcyclopentasiloxane and dodecamethylcyclohexasiloxane mixtures formed from hexamethyldisiloxane, octamethyltrisiloxane and decamethyltetrasiloxane particularly preferably, decamethylcyclopentasiloxane.

It has been shown that a proportion by weight of silicone oils with respect to the total weight of the antiperspirant stick of from about 25% to about 60% by weight, preferably from about 30% to about 50% by weight and in particular from about 35% to about 45% by weight is advantageous.

Further preferred cosmetic oils as contemplated herein are selected from the addition products of at least about 6 ethylene oxide and/or propylene oxide units to mono- or multivalent C3-22 alkanols, in particular glycerine, butanol, butanediol, myristyl alcohol and stearyl alcohol, which may optionally be esterified, for example PPG-14 butyl ether (Ucon Fluid® AP), PPG-9 butyl ether (Breox® B25), PPG-10 butanediol (Macol® 57), PPG-15 stearyl ether (Arlamol® E) and glycereth-7-diisononanoate. Particularly preferably, oils from the PPG-14 butyl ether group are used.

Cosmetically advantageous antiperspirant sticks have a proportion by weight of hydrophobic carrier material selected from the group formed by addition products of at least about 6 ethylene oxide and/or propylene oxide units to mono- or multivalent C3-22 alkanols with respect to their total weight of from about 8.0% to about 24% by weight, preferably from about 10% to about 21% by weight and in particular from about 12% to about 18% by weight.

A further preferred component of the hydrophobic carrier material is constituted by fatty components which are solid under normal conditions with a melting point of at least about 50° C. Preferred solid fatty components are those selected from the group formed by fatty alcohols, preferably from saturated C10-C22 fatty alcohols, in particular from fatty alcohols from the group formed by stearyl alcohol, cetyl alcohol and arachidyl alcohol.

The addition of solid fatty components, for example the fatty alcohols described above, serves in particular to thicken the hydrophobic carrier material, but also to adjust the payout properties of the antiperspirant stick. In respect of their thickening and payout properties, those antiperspirant sticks which have a proportion by weight of hydrophobic carrier material selected from the fatty alcohol group with respect to the total weight of the antiperspirant stick of from about 12% to about 35% by weight, preferably from about 15% to about 30% by weight and in particular from about 16% to about 27% by weight, have proved to be advantageous.

In summary, a particularly preferred antiperspirant stick contains, with respect to its total weight (A) from about 5.0% to about 20% by weight of aluminium zirconium trichlorohydrex glycine (B) hydrophobic carrier material, comprising from about 30% to about 50% by weight of decamethylcyclopentasiloxane from about 16% to about 27% by weight of fatty alcohol from the group formed by stearyl alcohol, cetyl alcohol and arachidyl alcohol from about 12% to about 18% by weight of PPG-14 butyl ether (C) from about 0.3% to about 1.0% by weight of behenyl behenate (D) from about 0.3% to about 1.0% by weight of behenate from the group formed by cetyl behenate and stearyl behenate, wherein the ratio of the proportion by weight of the behenyl behenate (C) with respect to the total weight of the antiperspirant stick to the proportion by weight of the behenate from the group formed by cetyl behenate and stearyl behenate (D) with respect to the total weight of the antiperspirant stick is from about 2:1 to about 1:2.

The following tables show the compositions of some preferred antiperspirant sticks (unless otherwise indicated, details are given as a % by weight with respect to the total weight of the antiperspirant stick).

|  | Formula 1 | Formula 2 | Formula 3 | Formula 4 |
|---|---|---|---|---|
| Perspiration-inhibiting substance * | 0.1 to 35 | 2.0 to 25 | 2.0 to 25 | 5.0 to 20 |
| Hydrophobic carrier material | 45 to 95 | 55 to 90 | 60 to 85 | 65 to 85 |
| Behenyl behenate ** | 0.1 to 4.0 | 0.2 to 2.0 | 0.2 to 2.0 | 0.3 to 1.0 |
| Behenate from the group formed by cetyl behenate and stearyl behenate | 0.1 to 4.0 | 0.2 to 2.0 | 0.2 to 2.0 | 0.3 to 1.0 |
| Misc | ad 100 | ad 100 | ad 100 | ad 100 |

* from the group formed by aluminium or aluminium-zirconium salts
** proportion by weight of behenyl behenate to cetyl behenate/stearyl behenate is from about 4:1 to about 1:4, preferably from about 2:1 to about 1:2 and in particular from about 4:3 to about 3:4

|  | Formula 6 | Formula 7 | Formula 8 | Formula 9 |
|---|---|---|---|---|
| Aluminium-zirconium trichlorohydrex glycine | 0.1 to 35 | 2.0 to 25 | 2.0 to 25 | 5.0 to 20 |
| Hydrophobic carrier material | 45 to 95 | 55 to 90 | 60 to 85 | 65 to 85 |
| Behenyl behenate ** | 0.1 to 4.0 | 0.2 to 2.0 | 0.2 to 2.0 | 0.3 to 1.0 |
| Behenate from the group formed by cetyl behenate and stearyl behenate | 0.1 to 4.0 | 0.2 to 2.0 | 0.2 to 2.0 | 0.3 to 1.0 |
| Misc | ad 100 | ad 100 | ad 100 | ad 100 |

** proportion by weight of behenyl behenate to cetyl behenate/stearyl behenate is from about 4:1 to about 1:4, preferably from about 2:1 to about 1:2 and in particular from about 4:3 to about 3:4

|  | Formula 11 | Formula 12 | Formula 13 | Formula 14 |
|---|---|---|---|---|
| Perspiration-inhibiting substance * | 0.1 to 35 | 2.0 to 25 | 2.0 to 25 | 5.0 to 20 |
| Silicone oil | 25 to 80 | 25 to 80 | 30 to 70 | 40 to 60 |
| Fatty alcohol *** | 12 to 35 | 15 to 30 | 15 to 30 | 16 to 27 |
| Behenyl behenate ** | 0.1 to 4.0 | 0.2 to 2.0 | 0.2 to 2.0 | 0.3 to 1.0 |
| Behenate from the group formed by cetyl behenate and stearyl behenate | 0.1 to 4.0 | 0.2 to 2.0 | 0.2 to 2.0 | 0.3 to 1.0 |
| Misc | ad 100 | ad 100 | ad 100 | ad 100 |

* from the group formed by aluminium or aluminium-zirconium salts
** proportion by weight of behenyl behenate to cetyl behenate/stearyl behenate is from about 4:1 to about 1:4, preferably from about 2:1 to about 1:2 and in particular from about 4:3 to about 3:4
*** from the group formed by stearyl alcohol, cetyl alcohol and arachidyl alcohol

|  | Formula 16 | Formula 17 | Formula 18 | Formula 19 |
|---|---|---|---|---|
| Perspiration-inhibiting substance * | 0.1 to 35 | 2.0 to 25 | 2.0 to 25 | 5.0 to 20 |
| Cyclopentasiloxane | 25 to 80 | 25 to 80 | 30 to 70 | 40 to 60 |
| Fatty alcohol *** | 12 to 35 | 15 to 30 | 15 to 30 | 16 to 27 |
| Behenyl behenate ** | 0.1 to 4.0 | 0.2 to 2.0 | 0.2 to 2.0 | 0.3 to 1.0 |
| Behenate from the group formed by cetyl behenate and stearyl behenate | 0.1 to 4.0 | 0.2 to 2.0 | 0.2 to 2.0 | 0.3 to 1.0 |
| Misc | ad 100 | ad 100 | ad 100 | ad 100 |

* from the group formed by aluminium or aluminium-zirconium salts
** proportion by weight of behenyl behenate to cetyl behenate/stearyl behenate is from about 4:1 to about 1:4, preferably from about 2:1 to about 1:2 and in particular from about 4:3 to about 3:4
*** from the group formed by stearyl alcohol, cetyl alcohol and arachidyl alcohol

|  | Formula 21 | Formula 22 | Formula 23 | Formula 24 |
|---|---|---|---|---|
| Aluminium-zirconium trichlorohydrex glycine | 0.1 to 35 | 2.0 to 25 | 2.0 to 25 | 5.0 to 20 |
| Silicone oil | 25 to 80 | 25 to 80 | 30 to 70 | 40 to 60 |
| Fatty alcohol *** | 12 to 35 | 15 to 30 | 15 to 30 | 16 to 27 |
| Behenyl behenate ** | 0.1 to 4.0 | 0.2 to 2.0 | 0.2 to 2.0 | 0.3 to 1.0 |
| Behenate from the group formed by cetyl behenate and stearyl behenate | 0.1 to 4.0 | 0.2 to 2.0 | 0.2 to 2.0 | 0.3 to 1.0 |
| Misc | ad 100 | ad 100 | ad 100 | ad 100 |

** proportion by weight of behenyl behenate to cetyl behenate/stearyl behenate is from about 4:1 to about 1:4, preferably from about 2:1 to about 1:2 and in particular from about 4:3 to about 3:4
*** from the group formed by stearyl alcohol, cetyl alcohol and arachidyl alcohol

|  | Formula 26 | Formula 27 | Formula 28 | Formula 29 |
|---|---|---|---|---|
| Aluminium-zirconium trichlorohydrex glycine | 0.1 to 35 | 2.0 to 25 | 2.0 to 25 | 5.0 to 20 |
| Cyclopentasiloxane | 25 to 80 | 25 to 80 | 30 to 70 | 40 to 60 |
| Fatty alcohol *** | 12 to 35 | 15 to 30 | 15 to 30 | 16 to 27 |
| Behenyl behenate ** | 0.1 to 4.0 | 0.2 to 2.0 | 0.2 to 2.0 | 0.3 to 1.0 |
| Behenate from the group formed by cetyl behenate and stearyl behenate | 0.1 to 4.0 | 0.2 to 2.0 | 0.2 to 2.0 | 0.3 to 1.0 |
| Misc | ad 100 | ad 100 | ad 100 | ad 100 |

** proportion by weight of behenyl behenate to cetyl behenate/stearyl behenate is from about 4:1 to about 1:4, preferably from about 2:1 to about 1:2 and in particular from about 4:3 to about 3:4
*** from the group formed by stearyl alcohol, cetyl alcohol and arachidyl alcohol

|  | Formula 31 | Formula 32 | Formula 33 | Formula 34 |
|---|---|---|---|---|
| Perspiration-inhibiting substance * | 0.1 to 35 | 2.0 to 25 | 2.0 to 25 | 5.0 to 20 |
| Silicone oil | 25 to 60 | 25 to 60 | 30% to 50 | 35 to 45 |
| Fatty alcohol *** | 12 to 35 | 15 to 30 | 15 to 30 | 16 to 27 |
| PPG-14 butyl ether | 8 to 24 | 10 to 21 | 10 to 21 | 12 to 18 |
| Behenyl behenate ** | 0.1 to 4.0 | 0.2 to 2.0 | 0.2 to 2.0 | 0.3 to 1.0 |
| Behenate from the group formed by cetyl behenate and stearyl behenate | 0.1 to 4.0 | 0.2 to 2.0 | 0.2 to 2.0 | 0.3 to 1.0 |
| Misc | ad 100 | ad 100 | ad 100 | ad 100 |

* from the group formed by aluminium or aluminium-zirconium salts
** proportion by weight of behenyl behenate to cetyl behenate/stearyl behenate is from about 4:1 to about 1:4, preferably from about 2:1 to about 1:2 and in particular from about 4:3 to about 3:4
*** from the group formed by stearyl alcohol, cetyl alcohol and arachidyl alcohol

|  | Formula 36 | Formula 37 | Formula 38 | Formula 39 |
|---|---|---|---|---|
| Aluminium-zirconium trichlorohydrex glycine | 0.1 to 35 | 2.0 to 25 | 2.0 to 25 | 5.0 to 20 |
| Silicone oil | 25 to 60 | 25 to 60 | 30 to 50 | 35 to 45 |
| Fatty alcohol *** | 12 to 35 | 15 to 30 | 15 to 30 | 16 to 27 |
| PPG-14 butyl ether | 8 to 24 | 10 to 21 | 10 to 21 | 12 to 18 |
| Behenyl behenate ** | 0.1 to 4.0 | 0.2 to 2.0 | 0.2 to 2.0 | 0.3 to 1.0 |
| Behenate from the group formed by cetyl behenate and stearyl behenate | 0.1 to 4.0 | 0.2 to 2.0 | 0.2 to 2.0 | 0.3 to 1.0 |
| Misc | ad 100 | ad 100 | ad 100 | ad 100 |

** proportion by weight of behenyl behenate to cetyl behenate/stearyl behenate is from about 4:1 to about 1:4, preferably from about 2:1 to about 1:2 and in particular from about 4:3 to about 3:4
*** from the group formed by stearyl alcohol, cetyl alcohol and arachidyl alcohol

|  | Formula 41 | Formula 42 | Formula 43 | Formula 44 |
|---|---|---|---|---|
| Perspiration-inhibiting substance * | 0.1 to 35 | 2.0 to 25 | 2.0 to 25 | 5.0 to 20 |
| Cyclopentasiloxane | 25 to 60 | 25 to 60 | 30 to 50 | 35 to 45 |
| Fatty alcohol *** | 12 to 35 | 15 to 30 | 15 to 30 | 16 to 27 |
| PPG-14 butyl ether | 8 to 24 | 10 to 21 | 10 to 21 | 12 to 18 |
| Behenyl behenate ** | 0.1 to 4.0 | 0.2 to 2.0 | 0.2 to 2.0 | 0.3 to 1.0 |
| Behenate from the group formed by cetyl behenate and stearyl behenate | 0.1 to 4.0 | 0.2 to 2.0 | 0.2 to 2.0 | 0.3 to 1.0 |
| Misc | ad 100 | ad 100 | ad 100 | ad 100 |

* from the group formed by aluminium or aluminium-zirconium salts
** proportion by weight of behenyl behenate to cetyl behenate/stearyl behenate is from about 4:1 to about 1:4, preferably from about 2:1 to about 1:2 and in particular from about 4:3 to about 3:4
*** from the group formed by stearyl alcohol, cetyl alcohol and arachidyl alcohol

|  | Formula 41 | Formula 42 | Formula 43 | Formula 44 |
|---|---|---|---|---|
| Aluminium-zirconium trichlorohydrex glycine | 0.1 to 35 | 2.0 to 25 | 2.0 to 25 | 5.0 to 20 |
| Cyclopentasiloxane | 25 to 60 | 25 to 60 | 30 to 50 | 35 to 45 |
| Fatty alcohol *** | 12 to 35 | 15 to 30 | 15 to 30 | 16 to 27 |
| PPG-14 butyl ether | 8 to 24 | 10 to 21 | 10 to 21 | 12 to 18 |
| Behenyl behenate ** | 0.1 to 4.0 | 0.2 to 2.0 | 0.2 to 2.0 | 0.3 to 1.0 |
| Behenate from the group formed by cetyl behenate and stearyl behenate | 0.1 to 4.0 | 0.2 to 2.0 | 0.2 to 2.0 | 0.3 to 1.0 |
| Misc | ad 100 | ad 100 | ad 100 | ad 100 |

** proportion by weight of behenyl behenate to cetyl behenate/stearyl behenate is from about 4:1 to about 1:4, preferably from about 2:1 to about 1:2 and in particular from about 4:3 to about 3:4
*** from the group formed by stearyl alcohol, cetyl alcohol and arachidyl alcohol In addition to the ingredients described above, the antiperspirant sticks may contain further substances and auxiliary substances.

The group of further substances includes fragrance and aromatic substances which, in the context of this application, are not included in the group of hydrophobic carrier materials.

Preferably, mixtures of different fragrances are used which together produce an appropriate perfume note. Suitable perfume oils may also contain natural aromatic substance mixtures which can be obtained from plant or animal sources, for example pine, citrus, jasmine, rose, lily or ylang-ylang oils. Ether oils with a low volatililty, which are mainly used as aroma components, are also suitable as perfume oils, for example sage oil, chamomile oil, melissa oil, peppermint oil, cinnamon leaf oil, linden blossom oil, juniper berry oil, vetiver oil, olibanum oil, galbanum oil, laudanum oil, clove oil, iso-eugenol, thyme oil, bergamot oil, geranium oil and rose oil.

Furthermore, the antiperspirant stick may contain additional deodorizing substances. Antimicrobial, antibacterial or bacteriostatic substances, antioxidants or odour-absorbing substances (for example zinc ricinoleate) may be used as the deodorizing substances. Particular suitable antimicrobial, antibacterial or bacteriostatic substances are organohalogen compounds as well as halides, quaternary ammonium compounds, a series of plant extracts and zinc compounds. Preferred substances are halogenated phenol derivatives such as, for example, hexachlorophene or Irgasan DP 300 (triclosan, 2,4,4'-trichloro-2'-hydroxydiphenylether), 3,4,4'-trichlorocarbonilide, chlorhexidine (1,1'-hexamethylene-bis-[5-(4-chlorophenyl)]-biguanide), chlorhexidine gluconate, benzalkonium halides and cetyl pyridinium chloride. Furthermore, sodium bicarbonate, sodium phenolsulphonate and zinc phenolsulphonate as well as, for example, the components of linden blossom oils, may also be used. Even weakly effective antimicrobial substances which, however, have a specific action against the gram positive bacteria responsible for perspiration decomposition, may be used as deodorizing substances. In addition, benzyl alcohol may be used as a deodorizing substance. Further antibacterially effective deodorants are lantibiotics, glycoglycerolipids, sphingolipids (ceramides), sterols and other substances which inhibit bacterial adhesion to the skin, for example glycosidases, lipases, proteases, carbohydrates, di- and oligosaccharide fatty acid esters as well as alkylated mono- and oligosaccharides. Preferred deodorizing substances are long-chain diols, for example 1,2-alkane-(C5-C18) diols, glycerine mono(C8-C18) fatty acid esters or, particularly preferably, glycerine mono-(C6-C16) alkylethers, in particular 2-ethylhexylglycerine ethers, which are very skin and mucous membrane-friendly and active against corynebacteria, as well as, furthermore, phenoxyethanol, phenoxyisopropanol (3-phenoxy-propan-2-ol), anisylic alcohol, 2-methyl-5-phenyl-pentan-1-ol, 1,1-dimethyl-3-phenyl-propan-1-ol, benzyl alcohol, 2-phenylethan-1-ol, 3-phenylpropan-1-ol, 4-phenylbutan-1-ol, 5-phenylpentan-1-ol, 2-benzylheptan-1-ol, 2,2-dimethyl-3-phenylpropan-1-ol, 2,2-dimethyl-3-(3'-methylphenyl)-propan-1-ol, 2-ethyl-3-phenylpropan-1-ol, 2-ethyl-3-(3'-methylphenyl)-propan-1-ol, 3-(3'-chlorophenyl)-2-ethylpropan-1-ol, 3-(2'-chlorophenyl)-2-ethylpropan-1-ol, 3-(4'-chlorophenyl)-2-ethylpropan-1-ol, 3-(3',4'-dichlorophenyl)-2-ethylpropan-1-ol, 2-ethyl-3-(2'-methylphenyl)-propan-1-ol, 2-ethyl-3-(4'-methylphenyl)-propan-1-ol, 3-(3',4'-dimethylphenyl)-2-ethylpropan-1-ol, 2-ethyl-3-(4'-methoxyphenyl)-propan-1-ol, 3-(3',4'-dimethoxyphenyl)-2-ethylpropan-1-ol, 2-allyl-3-phenylpropan-1-ol and 2-n-pentyl-3-phenylpropan-1-ol.

The antiperspirant sticks may also contain fillers. These fillers are typically selected from the group formed by talc, cellulose powder, starch and starch derivatives. Particularly preferably, talc is used.

In a further aspect, the present application concerns a non-therapeutic, cosmetic method for reducing and/or regulating the formation of perspiration and/or of body odour, in which a compound as contemplated herein or preferred as contemplated herein is applied to the skin in an effective quantity, preferably to the skin in the region of the armpit.

Further preferred embodiments of the method as contemplated herein can be obtained mutatis mutandis from the recitals relating to the compositions.

EXAMPLES

In order to produce the antiperspirant suspensions, the oil-soluble ingredients shown in the table below were dissolved in cyclopentasiloxane at about 80° C. and the powder to be dispersed was added at about 60° C.

|  | V1 | V2 | V3 | V4 | E1 |
|---|---|---|---|---|---|
| Aluminium-zirconium trichlorohydrex glycine | 17.8 | 17.8 | 17.8 | 17.8 | 17.8 |
| Stearyl alcohol | 22.0 | 22.0 | 22.0 | 22.0 | 22.0 |
| Cetyl alcohol | 0.4 | 0.4 | 0.4 | 0.4 | 0.4 |
| Arachidyl alcohol | 0.1 | 0.1 | 0.1 | 0.1 | 0.1 |
| Talc | 3.0 | 3.0 | 3.0 | 3.0 | 3.0 |
| Hydrogenated castor oil | 2.8 | 2.8 | 2.8 | 2.8 | 2.8 |
| PPG-14 butyl ether | 14.0 | 14.0 | 14.0 | 14.0 | 14.0 |
| Behenyl behenate | — | — | 1.0 | — | 0.5 |
| Cetearyl behenate | — | — | — | 1.0 | 0.5 |
| Synthetic paraffin wax | 1.0 | — | — | — | — |
| Myristyl myristate | — | 1.0 | — | — | — |
| Cyclopentasiloxane | ad 100 | ad 100 | ad 100 | ad 100 | ad 100 |

The physical stability and sensorial properties of the antiperspirant suspensions, formed into sticks, were then investigated. The stick hardness was measured using a penetrometer (about 45° cone, about 0.5 mm penetration depth).

|  | V1 | V2 | V3 | V4 | E1 |
|---|---|---|---|---|---|
| Synaeresis after 3 weeks (0° C.) | no | yes | no | no | no |
| Stick hardness (g) | n.d. | 350 | 558 | 583 | 137 |
| Sensorial properties | n.d. | acceptable hardness and payout | too hard, low payout | too hard, low payout | creamy texture, good payout |

Surprisingly, only composition E provided optimal stability and stick hardness.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

What is claimed is:

1. An antiperspirant stick consisting of, with respect to its total weight: (A) from about 5.0% to about 20% by weight of aluminium zirconium trichlorohydrex glycine; (B) a hydrophobic carrier material, consisting of: from about 30% to about 50% by weight of cyclopentasiloxane; from about 16% to about 27% by weight of a fatty alcohol consisting of stearyl alcohol, cetyl alcohol and arachidyl alcohol; from about 12% to about 18% by weight of PPG-14 butyl ether; (C) 0.5% by weight of behenyl behenate; (D) 0.5% by weight of cetearyl behenate; (E) about 3% by weight of talc; and (F) from about 2% to about 3% by weight of hydrogenated castor oil.

2. The antiperspirant stick of claim 1 wherein the (A) aluminium zirconium trichlorohydrex glycine is present in an amount of about from about 17 to about 18% by weight.

3. The antiperspirant stick of claim 1 wherein the cyclopentasiloxane is present in an amount of from about 38 to about 39% by weight.

4. The antiperspirant stick of claim 1 wherein stearyl alcohol is present in an amount of about 22% by weight.

5. The antiperspirant stick of claim 1 wherein the cetyl alcohol is present in an amount of about 0.4% by weight.

6. The antiperspirant stick of claim 1 wherein the arachidyl alcohol is present in an amount of about 0.1% by weight.

7. The antiperspirant stick of claim 1 wherein the PPG-14 butyl ether is present in an amount of about 14% by weight.

8. The antiperspirant stick of claim 1 wherein the behenyl behenate is present in an amount of about 0.5% by weight.

9. The antiperspirant stick of claim 1 wherein the cetearyl behenate is present in an amount of about 0.5% by weight.

10. The antiperspirant stick of claim 1 having a hardness of about 137 g as measured using a penetrometer with about a 45° cone and about 0.5 mm penetration depth.

11. The antiperspirant stick of claim 1 wherein the cyclopentasiloxane is present in an amount of from about 38 to about 39% by weight, wherein the (A) aluminium zirconium trichlorohydrex glycine is present in an amount of about from about 17 to about 18% by weight, wherein stearyl alcohol is present in an amount of about 22% by weight, wherein the cetyl alcohol is present in an amount of about 0.4% by weight, wherein the arachidyl alcohol is present in an amount of about 0.1% by weight, wherein the PPG-14 butyl ether is present in an amount of about 14% by weight, wherein the behenyl behenate is present in an amount of about 0.5% by weight, and wherein the cetearyl behenate is present in an amount of about 0.5% by weight.

12. The antiperspirant stick of claim 11 having a hardness of about 137 g as measured using a penetrometer with about a 45° cone and about 0.5 mm penetration depth.

13. An antiperspirant stick consisting of, with respect to its total weight:
17.8% by weight of aluminium zirconium trichlorohydrex glycine;
22% by weight of stearyl alcohol;
0.4% by weight of cetyl alcohol;
0.1% by weight of arachidyl alcohol;
3% by weight of talc;
2.8% by weight of hydrogenated castor oil;
14% by weight of PPG-14 butyl ether;
0.5% by weight of behenyl behenate;
0.5% by weight of cetearyl behenate; and
38.9% by weight of cyclopentasiloxane.

14. The antiperspirant stick of claim 13 having a hardness of about 137 g as measured using a penetrometer with about a 45° cone and about 0.5 mm penetration depth.

15. A non-therapeutic, cosmetic method for reducing and/or regulating the formation of perspiration and/or of body odour, in which a composition as claimed in claim 1 is applied to the skin in an effective quantity.

* * * * *